(12) United States Patent
Mullejans et al.

(10) Patent No.: US 7,722,586 B2
(45) Date of Patent: May 25, 2010

(54) OSTOMY APPLIANCE

(75) Inventors: Peter Mullejans, Aalsgaarde (DK); Michael Hansen, Gilleleje (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 10/549,567

(22) PCT Filed: Mar. 12, 2004

(86) PCT No.: PCT/DK2004/000157
§ 371 (c)(1), (2), (4) Date: Sep. 19, 2005

(87) PCT Pub. No.: WO2004/082452
PCT Pub. Date: Sep. 30, 2004

(65) Prior Publication Data
US 2006/0200101 A1    Sep. 7, 2006

(30) Foreign Application Priority Data
Mar. 17, 2003    (DK) ............................... 2003 00409

(51) Int. Cl.
*A61F 5/44* (2006.01)
(52) U.S. Cl. .................. 604/342; 604/332; 604/337; 604/338; 604/339; 604/341
(58) Field of Classification Search .......... 604/332–345
See application file for complete search history.

(56) References Cited

U.S. PATENT DOCUMENTS 4,367,732 A    1/1983   Poulsen et al.

(Continued)

FOREIGN PATENT DOCUMENTS

CA    1 108 958    9/1981

(Continued)

OTHER PUBLICATIONS

English translation of the specification of DE 19519069 from EPO website http://v3.espacenet.com/textdes?DB=EPODOC&IDX=DE19519069&F=0&QPN=DE19519069.*

*Primary Examiner*—Melanie J Hand
(74) *Attorney, Agent, or Firm*—Jacobson Holman PLLC (57) ABSTRACT

An ostomy appliance comprising a base plate, said base plate having a first hole for receiving a stoma, ureter, or catheter and an adhesive wafer having a first surface to be attached to the wearer's abdomen back, or chest; a receiving member or bag releasably attached to the base plate, said bag having a second hole for receiving wastes exiting the stoma, ureter or catheter; and a disposable inner bag liner forming a second bag inside the receiving member and being releasably attachable to the base plate in a first coupling area by first coupling means, said disposable inner bag liner having a third hole for receiving wastes exiting the stoma, ureter or catheter and the receiving wastes exiting the stoma, ureter or catheter and the receiving member being releasably attachable to the base plate by second coupling means wherein the first coupling means is in the form of an adhesive flange projecting from the rim of the third hole and having a surface for releasable sealing against a second surface of the base plate facing away from the user provides an ostomy appliance combining the advantages of using a separate, flushable inner bags with an easy, safe, hygienic and discreet management of the collected waste with maximum safety against soiling parts of the appliance not to be substituted when substituting the inner bag, which inner bag may be used directly together with existing ostomy devices.

13 Claims, 4 Drawing Sheets

U.S. PATENT DOCUMENTS

| | | | |
|---|---|---|---|
| 4,449,970 A | 5/1984 | Bevan et al. | |
| 4,710,183 A | 12/1987 | Steer | |
| 4,714,465 A | 12/1987 | Steer | |
| 4,816,027 A | 3/1989 | Gilchrist et al. | |
| 5,051,259 A | 9/1991 | Olsen et al. | |
| 5,209,744 A | 5/1993 | Abe et al. | |
| 5,306,264 A | 4/1994 | Ferguson et al. | |
| 5,423,782 A * | 6/1995 | Wolrich | 604/339 |
| 5,426,782 A | 6/1995 | Shiga | |
| 5,496,297 A | 3/1996 | Olsen | |
| 5,591,144 A * | 1/1997 | Smith et al. | 604/327 |
| 5,690,622 A | 11/1997 | Smith et al. | |
| 5,690,623 A | 11/1997 | Lenz et al. | |
| 5,714,225 A | 2/1998 | Hansen et al. | |
| 5,785,695 A | 7/1998 | Sato et al. | |
| 5,800,415 A | 9/1998 | Olsen | |
| 5,865,819 A | 2/1999 | Cisko, Jr. et al. | |
| 5,938,647 A | 8/1999 | Smith | |
| 6,171,594 B1 | 1/2001 | Nielsen | |
| 6,303,700 B1 | 10/2001 | Chen | |
| 6,312,415 B1 | 11/2001 | Nielsen et al. | |
| 6,437,038 B1 | 8/2002 | Chen | |
| 6,451,883 B1 | 9/2002 | Chen et al. | |
| 6,685,683 B1 | 2/2004 | Clok et al. | |
| 2004/0064132 A1 * | 4/2004 | Boehringer et al. | 604/543 |

FOREIGN PATENT DOCUMENTS

| | | |
|---|---|---|
| DE | 1 947 368 | 4/1971 |
| DE | 195 19 069 A1 | 11/1996 |
| DE | 19519069 A1 * | 11/1996 |
| DE | 199 21 555 A1 | 2/2000 |
| DE | 203 08 266 U1 | 8/2003 |
| DE | 20 2004 000 323 U1 | 5/2004 |
| EP | 0 259 184 B1 | 3/1988 |
| EP | 0 320 895 A1 | 6/1989 |
| EP | 0 703 762 | 4/1996 |
| EP | 0 747 026 B1 | 12/1996 |
| EP | 0 768 848 | 4/1997 |
| EP | 0 768 849 | 4/1997 |
| EP | 0 821 925 A2 | 2/1998 |
| EP | 1 290 994 A2 | 3/2003 |
| FR | 2 476 481 A1 | 8/1981 |
| GB | 2 265 832 A | 10/1993 |
| GB | 2 306 889 A | 5/1997 |
| HU | 190 848 | 11/1986 |
| WO | WO 91/01118 | 2/1991 |
| WO | WO 91/01119 | 2/1991 |
| WO | WO 93/18725 | 9/1993 |
| WO | WO 94/12128 | 6/1994 |
| WO | WO 94/18919 | 9/1994 |
| WO | WO 96/01090 | 1/1996 |
| WO | WO 96/01091 | 4/1997 |
| WO | WO 99/30652 | 6/1999 |
| WO | WO 00/30576 | 6/2000 |
| WO | WO 00/54820 | 9/2000 |
| WO | WO 00/67683 | 11/2000 |
| WO | WO 01/05340 A2 | 1/2001 |
| WO | WO 01/10363 A1 | 2/2001 |
| WO | WO 01/21115 A1 | 3/2001 |
| WO | WO 01/54632 A1 | 8/2001 |
| WO | WO 01/82846 A1 | 11/2001 |
| WO | WO 02/058603 A1 | 8/2002 |
| WO | WO 2004/082452 A2 | 9/2004 |

* cited by examiner

OSTOMY APPLIANCE

This is a nationalization of PCT/DK2004/000157 filed 12 Mar. 2004 and published in English.

BACKGROUND OF THE INVENTION

1. Field of the Invention

The present invention relates to an ostomy appliance comprising a receiving bag and a disposable bag liner and optionally a body side member, a disposable bag liner for use together with an ostomy appliance, and a method for applying such an ostomy appliance.

In connection with surgery for a number of diseases in the gastro-intestinal or urinary tract a consequence is, in many cases, that the colon, the ileum or the ureter has been exposed surgically and the patient is left with an abdominal stoma, or, in nephrostomy or ureterostomy, the ureter or a catheter is exposed in the back or the chest region or abdominal region, and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma/ureter/catheter. Also in connection with a fistula, the patient will have to rely on an appliance to collect the bodily material emerging from such opening.

Ostomy appliances are well known. Such appliances may be two-piece or one-piece appliances. In both types of appliances, an adhesive barrier member (or base plate) is attached to the wearer's abdomen/back/chest. In case of a one-piece appliance, a receiving member or bag is attached to the base plate. In case of a two-piece appliance, the adhesive base plate forms part of a body side member and a receiving member or bag is attached releasably to the body side member for receiving exudates from the stoma.

When using one-piece appliances, the whole appliance, including the adhesive skin barrier securing the appliance to the skin is normally removed and replaced by a fresh appliance. When using two-piece appliances, the body side ostomy member is left in place up to several days, and only the receiving member or bag attached to the body side member is replaced. The attachment means for attaching an ostomy receiving bag may be a system known per se comprising matching coupling rings or matching flanges and adhesive surfaces engaging with and sealing against a flange area of the body side member.

A known major problem with receiving bags is that it can be difficult to dispose of the used bag in a convenient and hygienic manner. Some ostomates will cut the used bags open, e.g. by cutting off an edge thereof and depositing the contents into a WC for flushing away and disposing or depositing the empty bag in a waste bin. Such disposal of used bags and the contents therein is indeed unhygienic and undesirable for the user, especially in public rest rooms, and in view of this a number of proposals have been made for ostomy bags which may be flushed down e.g. a WC.

2. Description of the Related Art

Thus, U.S. Pat. No. 5,423,782 (Wolrich) discloses a disposable ostomy bag liner apparatus including a unitary flexible bag having a main body portion, a tapered 20 portion and a flange portion in which the tapered portion is disposed adjacent the main body portion and together, the main body portion and tapered portion define an interior portion of the bag for receiving and hold intestinal waste material. The patent discloses a bag liner for use by colostomy and some ileostomy patients which is easy to install in a conventional ostomy bag, which has provisions to allow for escape of gas admitted into the liner and which is relatively inexpensive to produce.

EP Patent No. 0 768 848 (Welland Medical Limited) discloses a biodegradable, flushable ostomy bag liner comprising inner walls formed from polyvinylacetate/polyvinylalcohol film of a grade which disintegrates within 60 seconds in water at 50° C. but retains its structural integrity in water at 25° C. for at least two days, outer walls formed from a nonwoven fabric which disintegrates in water at 25° C., means defining an opening in the inner and outer walls for receiving bodily waste from the stoma patient, an adhesive flange being secured to at least an inner wall of the liner and surrounding the said opening, wherein the walls of the inner and outer bags are unconnected and form a non-laminar arrangement over the greater part of their area, but are connected around their peripheral margins and in the region of the adhesive flange.

EP Patent No. 0 703 762 (Welland Medical Limited) forms basis for the invention disclosed in EP Patent No. 0 768 848 above and discloses a drainage bag for receiving bodily waste, the drainage bag containing an outer bag, a water-impermeable inner bag enclosed within the outer bag, the inner bag being of a structure which is weakened upon immersion in a WC bowl such that it becomes limp and is less buoyant thereby enabling it to be flushed away easily, and means defining an orifice to enable bodily waste to be received by the inner bag in which the outer bag is water-impermeable and is formed from a material which acts as a barrier to flatus gases. The outer bag is provided with a flatus filter, the inner bag is permeable to flatus gases, and the outer and inner bags are detachably secured together in the region of the orifice.

GB Patent Application No. 2 306 889 (Alcare Co Ltd) discloses a body waste receiving appliance comprising an adhesive plate with an opening to a wastes discharge hole or opening formed on the surface of a human body, a first flange secured to the non-adhesive side of said adhesive plate and having an opening corresponding to the opening of said adhesive plate, a second flange detachably mounted at the opposite side, with reference to said adhesive plate, of said first flange and having an opening corresponding to the opening of said first flange, an outer pouch secured at the opposite side, with reference to the adhesive plate, of said second flange and having an opening corresponding to the respective openings of said adhesive plate, said first flange and said second flange, and an inner pouch for receiving the body wastes through the respective openings of said adhesive plate and said first flange, said inner pouch being housed inside the outer pouch in such a manner as to be separable therefrom, said outer pouch being formed of a non-water-soluble film, while said inner pouch being formed of a water-soluble film which is dissolved or disintegrated in water, said inner pouch being replaceable.

EP Patent Application No. 0 821 925 (Quacquarella) discloses an ostomy appliance comprising a reusable outer bag and a disposable inner bag, means for securing the two bags together and to the stoma, means for inserting and removing the inner bag from the outer bag, and means for closing the outer bag once the inner bag is in place.

In applicants own WO publication 01/82846 is disclosed an ostomy appliance comprising an adhesive barrier member (or base plate), said barrier member having a hole for receiving a stoma, ureter, or catheter and barrier wafer to be attached to the wearers abdomen, back, or chest; an outer receiving member or bag releasably attached to the adhesive barrier member, said bag having a hole for receiving wastes exiting the stoma, ureter or catheter; and a disposable inner bag liner releasably attached to the adhesive barrier member wherein the disposable inner bag liner having a hole for receiving wastes exiting the stoma, ureter or catheter is attached releasably to the adhesive barrier member in a first coupling area by first coupling means and the outer receiving member is attached releasably to the adhesive barrier member by second coupling means, in which the first and second coupling areas are in the form of one or more coupling rings and the first and second coupling means are in the form of matching coupling rings and wherein the outer diameter of the first coupling means is smaller than the inner diameter of the second coupling means.

The purpose of the present invention is to provide an ostomy appliance combining the advantages of using a separate, flushable inner bags with an easy, safe, hygienic and discreet management of the collected waste with maximum safety against soiling parts of the appliance not to be substituted when substituting the inner bag, which inner bag may be used directly together with existing ostomy devices.

SUMMARY OF THE INVENTION

The present invention relates to an ostomy appliance comprising a base plate, said base plate having a first hole for receiving a stoma, ureter, or catheter and an adhesive wafer having a first surface to be attached to the wearer's abdomen, back, or chest; a receiving member or bag releasably attached to the base plate, said bag having a second hole for receiving wastes exiting the stoma, ureter or catheter; and a disposable inner bag liner forming a bag inside the receiving member and being releasably attached to the base plate. The disposable inner bag liner has a third hole for receiving wastes exiting the stoma, ureter or catheter and is attached releasably to the base plate in a first coupling area by a first coupling component and the receiving member being attached releasably to the base plate by a second coupling component.

The present invention also relates to an ostomy appliance comprising an adhesive wafer, said adhesive wafer having a first hole for receiving a stoma, ureter, or catheter, said adhesive wafer having a first surface to be attached to the wearer's abdomen, back, or chest and a receiving member or bag attached to the base plate, said bag having a second hole for receiving wastes exiting the stoma, ureter or catheter; and a disposable inner bag liner forming a bag inside the receiving member and being releasably attached to the adhesive wafer. The disposable inner bag liner has a third hole for receiving wastes exiting the stoma, ureter or catheter and is attached releasably to the adhesive wafer in a first coupling area by a first coupling component.

Furthermore, the present invention relates to a disposable inner bag liner for receiving effluents or waste products of the body and for use together with an ostomy appliance comprising an adhesive wafer to be attached to the wearer's abdomen, back, or chest and a receiving member or bag having a hole for receiving wastes exiting the stoma, ureter or catheter. The disposable inner bag liner has a hole for receiving wastes exiting the stoma, ureter or catheter, is capable of forming a bag inside the receiving member and is releasably attachable to the adhesive wafer in a first coupling area by a first coupling component.

Still further the invention relates to a method of applying an ostomate an ostomy appliance.

BRIEF DESCRIPTION OF THE DRAWINGS

The invention is disclosed more in detail with reference to the drawings in which.

DETAILED DESCRIPTION OF THE PRESENT INVENTION

In its broadest aspect, the invention relates to a disposable inner bag liner in the form of disc-shaped member comprising a ring-shaped element and a compacted inner bag liner made from a flushable material and being located in the central part of the ring-shaped element.

The present invention relates in a FIRST ASPECT to an ostomy appliance comprising a base plate, said base plate having a first hole for receiving a stoma, ureter, or catheter and an adhesive wafer having a first surface to be attached to the wearer's abdomen, back, or chest; a receiving member or bag releasably attached to the base plate, said bag having a second hole for receiving wastes exiting the stoma, ureter or catheter; and a disposable inner bag liner forming a second bag inside the receiving member and being releasably attachable to the base plate in a first coupling area by a first coupling component. The, disposable inner bag liner has a third hole for receiving wastes exiting the stoma, ureter or catheter and the receiving member is releasably attachable to the base plate by a second coupling component, wherein the first coupling component is in the form of an adhesive flange projecting from the rim of the third hole and has a surface for releasable sealing against a second surface of the base plate facing away from the user.

In one embodiment of the present invention the second coupling component is in the form of an adhesive flange projecting from the rim of the second hole and having a surface for adhesive sealing against the second surface of the base plate. The second hole is provided in the flange of the receiving member. The outer diameter of the first coupling component preferably is greater than the inner diameter of the second coupling component which allows use together with coupling components in the form of matching adhesive flanges and also in the form of matching coupling rings.

It is suitable that the peel strength of the adhesive sealing of the first coupling component is greater than the peel strength of the second coupling component. This renders it easy to selectively detach the receiving member, leaving the inner bag liner attached to a base plate. This may be effected by providing the flange with release properties on the surface facing the receiving member.

In another embodiment of the invention, the second coupling component is in the form of one or more coupling rings wherein the outer diameter of the first coupling component is smaller than the inner diameter of the second coupling component.

When the inner bag liner stays attached to the base plate, it acts as a drip-catcher and while the user attaches a fresh inner bag liner to the receiving member which may be reused several times. The inner bag liner will thus reduce the risk of escaping odor or soiling of the clothing by dripping output from the stoma.

Thus, the user may easily flush the contents of the receiving member in the WC and is not left with a soiled receiving member but rather with a receiving member, which may be used again or be disposed in a waste bin without obnoxious smells.

This is especially advantageous for people living in flats and people bothered by leaving used ostomy bags giving rise to obnoxious smells in public toilets or at work or who might empty a used bag before disposing the same in the waste bin.

It is advantageous to provide the inner bag liner with a membrane allowing intestinal gas to escape from the inner bag but being impermeable to liquids in order to avoid ballooning. The use of an inner bag liner will in itself prolong the active service time of a filter of a receiving member as the contents of the receiving member is separated physically from the filter reducing the risk of blocking.

The inner bag liner may be used with all types of stomas but the advantages are most pronounced in connection with colostomies and in particular ileo-ostomies where the users typically exchange receiving members two to three times a day.

In a SECOND ASPECT, the present invention relates to an ostomy appliance comprising an adhesive wafer, said adhesive wafer having a first hole for receiving a stoma, ureter, or catheter, said adhesive wafer having a first surface to be attached to the wearer's abdomen, back, or chest and a receiving member or bag attached to the adhesive wafer. The bag has a second hole for receiving wastes exiting the stoma, ureter or catheter. A disposable inner bag liner forms a bag inside the receiving member and is releasably attachable to the adhesive wafer by a first coupling component, said disposable inner bag liner having a third hole for receiving wastes exiting the stoma, ureter or catheter wherein the first coupling component is in the form of an adhesive flange projecting from the rim of the third hole and having a surface for releasable sealing against a first surface of the adhesive wafer.

In a preferred embodiment of the present invention, the inner bag liner is compacted lengthwise to form a disc-like structure having an outer diameter less than the inner diameter of the first coupling component. Thus, a unit, which is simple to handle, is provided which may be used with existing ostomy equipment. The folding of the inner bag liner minimizes the risk of "pancaking" and blocking of the bag as the inner bag liner is automatically gradually unfolded or stretched by the output from the stoma first contacting the bottom of the inner bag liner and pressing the same down into the receiving bag bottom portion.

In one embodiment of the invention the inner bag liner is provided with folding lines for compacting the bag lengthwise. The folding lines may suitably form a bellows, which ensures that output from the stoma is disposed directly to the bottom of the inner bag liner causing an unfolding only exposing the sides thereof after filling the lower parts which reduces the risk of adherence to the sides of the inner bag liner.

In another embodiment of the invention the folding lines form a telescopic bellows giving a relatively narrow front when the inner bag liner expands into the receiving member.

For keeping the disc-shaped member in a compact conformation, for easy handling and for protecting the inner bag liner before use it is suitable to provide the closed end of the compacted inner bag liner with a cover.

In a third aspect, the present invention relates to a disposable inner bag liner for receiving effluents or waste products of the body and for use together with an ostomy appliance comprising an adhesive wafer to be attached to the wearer's abdomen, back, or chest and a receiving member having a hole for receiving wastes exiting the stoma, ureter or catheter, said disposable inner bag liner having a hole for receiving wastes exiting the stoma, ureter or catheter and being capable of forming a bag inside the receiving member for being releasably attachable to the adhesive wafer in a first coupling area by a first coupling component, wherein the first coupling component is in the form of an adhesive flange projecting from the rim of the hole and has a surface for releasable sealing against a surface of the adhesive wafer.

The disposable inner bag liner of the invention may be used together with existing ostomy devices one-piece ostomy appliances and also together with existing two-piece ostomy appliances, such as appliances comprising a base plate and a receiving member releasably attached via matching adhesive flanges or via matching coupling rings. A preferred such use is together with one-piece appliances or together with two-piece appliances wherein a base plate and a receiving member are attached via matching adhesive flanges. A disposable inner bag liner of the invention may be used together with appliances having very flexible such flanges without compromising the overall flexibility provided that the ring-shaped element and the flange show at approximately least the same flexibility as the adhesive flanges.

Thus, the inner bag liner is suitably made from a thin, water-impermeable sheet, which is not gas-tight. The bag liner is suitably in the form of a co-extruded or laminated sheet having a layer of water-soluble material such as PVA, PVAL or EVAL at the outer surface. The inner surface may suitably be made from a material, which may be processed into a thin layer without pinholes such as PE, EVA, PVC, PP, or a polyester which layer is impermeable for water vapour. The outer material may e.g. be in the form of a sheet or a non-woven material.

An inner bag liner of the invention may be made from a material being permeable for tight and thus permitting intestinal gasses entering the bag to diffuse through the inner bag liner without giving rise to ballooning for management by a conventional gas venting and filtering system placed on the outer bag. The inner bag liner is preferably impermeable to water and water vapour in order to avoid leaking of liquid or passing of water vapour which would start a deterioration of the outer layer of the bag liner.

An inner bag liner may be produced by a manner known per se for producing bags such as blowing and welding or by cutting separate walls which are then sealed along the rim in a manner known per se, e.g. using an adhesive or by welding. When producing the inner bag liner it is suitably taken into account to provide a shape, which is readily folded afterwards in a manner known per se for providing bellows or telescopic bellows.

In a fourth aspect, the present invention relates to a method of applying to an ostomate an ostomy appliance comprising a base plate, said base plate having a first hole for receiving a stoma, ureter, or catheter and an adhesive wafer having a first surface to be attached to the wearer's abdomen, back, or chest; a receiving member or bag releasably attachable to the base plate, said receiving member having a second hole for receiving wastes exiting the stoma, ureter or catheter; and a disposable inner bag liner forming a second bag inside the receiving member and being releasably attachable to the base plate. The disposable inner bag liner has a third hole for receiving wastes exiting the stoma, ureter or catheter, said inner bag liner being compacted lengthwise to form a disc-like structure, and said inner bag liner being attachable releasably to the base plate in a first coupling area by a first coupling component, and the receiving member being attachable releasably to the base plate by a second coupling component wherein the first coupling component is in the form of an adhesive flange projecting from the rim of the third hole and has a surface for adhesive sealing against a second surface of the base plate facing away from the user. The method includes locating the stoma and applying the base plate, placing the inner bag liner and applying and sealing the same to the first coupling area, removing the release liner covering the first coupling component, if present, and attaching the receiving member to the base plate.

An adhesive wafer for a body side member or of a 1-piece ostomy appliance bag according to the present invention may comprise a medical grade barrier adhesive known in art the such as the formulation being disclosed e.g. in U.S. Pat. Nos. 4,367,732, 5,051,259, 5,714,225, 6,171,594, 6,303,700, 6,451,883, or 6,437,038, or in WO Application Nos. 00/54820, or 01/05340. For a 2-piece ostomy appliance according to the present invention, the body side member and the receiving member are provided with matching coupling components.

A coupling component may be any system known per se for attaching receiving bags to ostomy body side members and may suitably be matching coupling rings of the type disclosed in WO 93/18725, WO 94/18919, WO 91/01118, WO 91/01119 or matching flanges for adhesive connection of the type disclosed in U.S. Pat. No. 5,800,415, WO 00/30576, or WO 01/54632.

A carrier sheet present on the surface of the adhesive wafer facing the bag may be any suitable thermoplastic material known per se for use in the preparation of ostomy appliances e.g. a foam, a non-woven layer or a polyurethane, polyethylene, polyester or polyamide suitable for attachment of a receiving member using an adhesive or by welding.

A collection bag may be made in analogy with and from materials conventionally used for the preparation of ostomy appliances. Such materials are suitably films composed of any suitable material, which is heat sealable and sufficiently impervious for unpleasant odours such as polyolefin films or combinations of such films, e.g. polyethylene or a co-extrudate of polyethylene and polyvinylidene chloride. Suitably the bag is made from front and rear walls welded in a manner known per se along the rim forming a bag. When cutting or punching the walls, an opening for receiving a stoma is suitably also punched in the wall to form the rear wall.

A protective cover or release liner may for instance be siliconized paper. The protective cover is not present during the use of the ostomy appliance of the invention and is therefore not an essential part of the invention.

DESCRIPTION OF THE PREFERRED EMBODIMENTS

The invention is now explained more in detail with reference to the drawings showing preferred embodiments of the invention.

Figure 1:
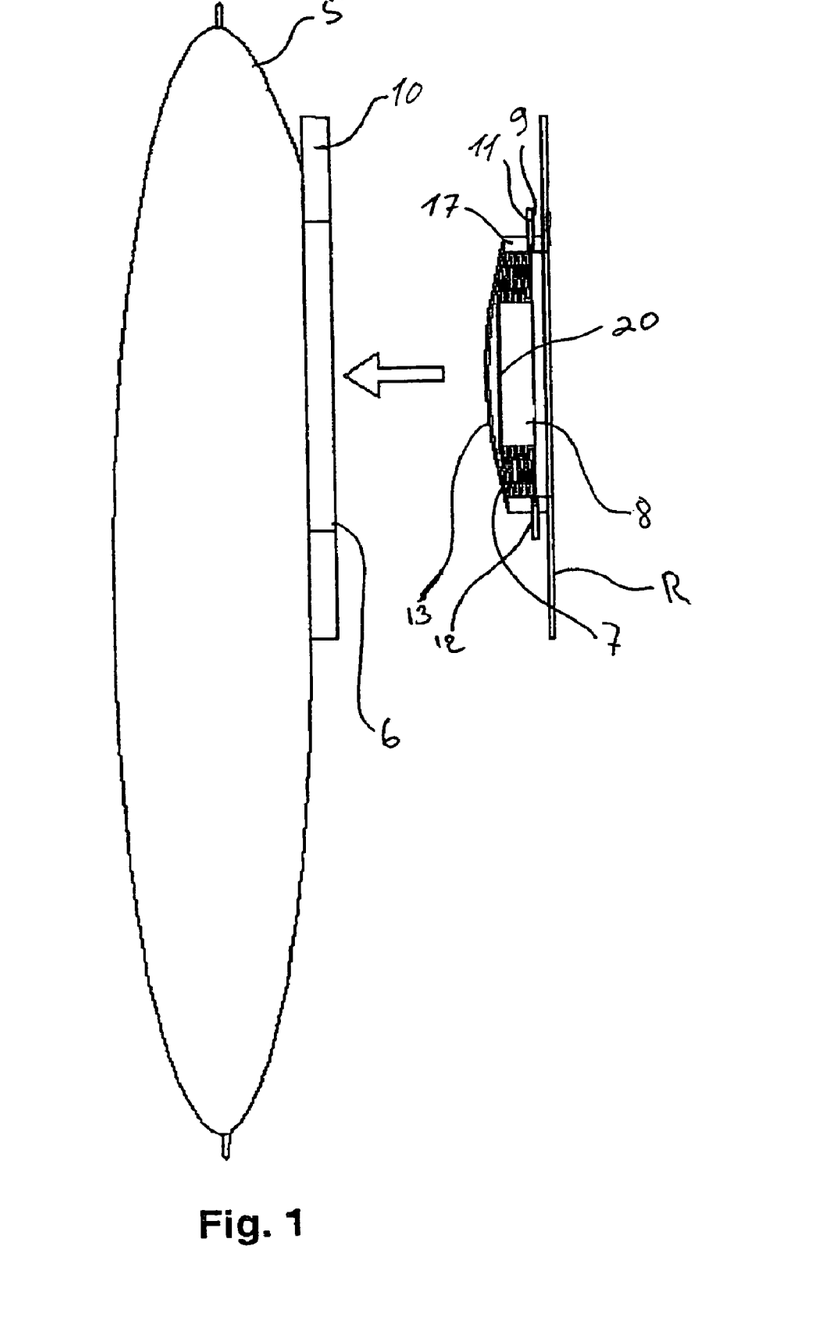
FIG. 1 shows parts of an embodiment of an ostomy appliance of the invention.
Figure 2:
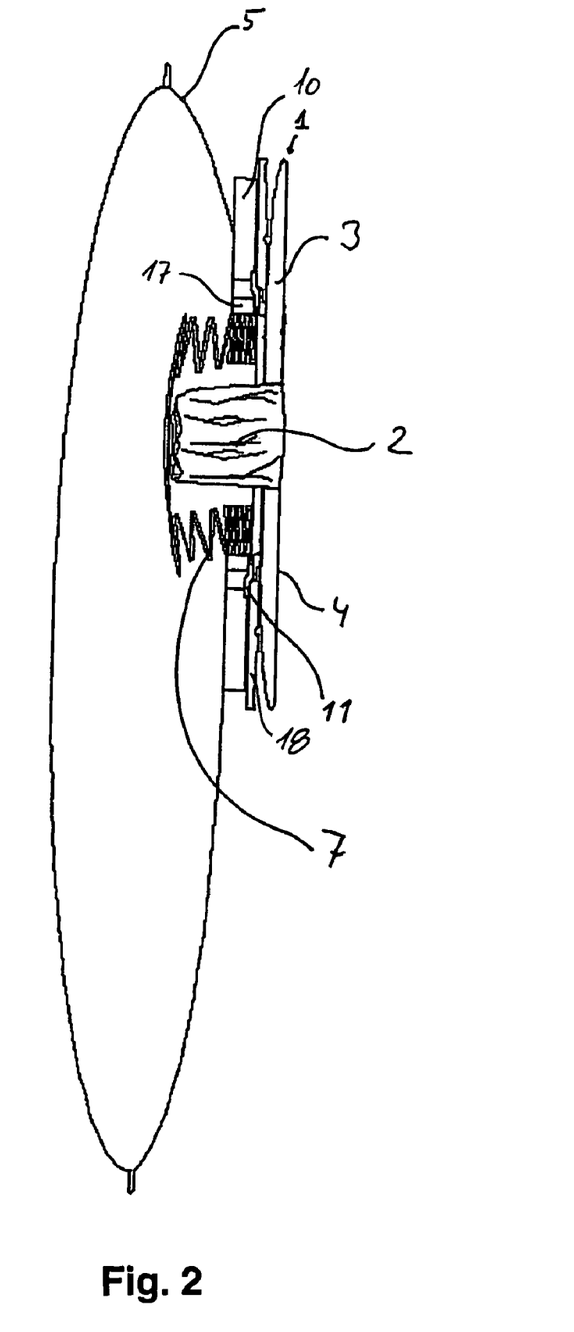
FIG. 2 shows the parts shown in FIG. 1 after assembly with a base plate and applied to the user's skin

Reference is made to FIGS. 1 and 2 showing an ostomy appliance comprising a base plate, said base plate 1 having a first hole for receiving a stoma 2, ureter, or catheter and an adhesive wafer 3 having a first surface 4 attached to the wearer's abdomen (not shown), back, or chest. A receiving member or bag 5 is releasably attached to the base plate, said bag having a second hole 6 for receiving wastes exiting the stoma, ureter or catheter; and a disposable inner bag liner 7 forming a second bag inside the receiving member and being releasably attached to the base plate. The disposable inner bag liner has a third hole 8 for receiving wastes exiting the stoma, ureter or catheter and is attached releasably to the base plate in a first coupling area 9 by a first coupling component and the receiving member is attached releasably to the base plate by a second coupling component in the form of an adhesive flange 10. The first coupling component is in the form of an adhesive flange 11 projecting from the rim of the third hole and has a surface for adhesive sealing against a second surface of the base plate facing away from the user and the flange 10.

In FIG. 1, the inner bag liner is shown in the form of a disc-shaped member in which the inner bag liner is compacted lengthwise with an inner bag liner bottom portion 20 constituting a closed end of said liner being covered by a cover 13 secured to the flange 11 and a release liner R covering the adhesive surface 9. In FIG. 1, the inner bag liner is shown in its compacted condition.

In FIG. 2 the inner bag liner and the receiving member are assembled and applied to a base plate placed on the user's skin (not shown) with the stoma projecting into the inner bag liner and the receiving member. As appears, the top of the stoma presses the inner bag liner into the receiving member. The flange 10 of the receiving member is adhesively secured and sealed to a flange 18 on the base plate.

Figure 3:
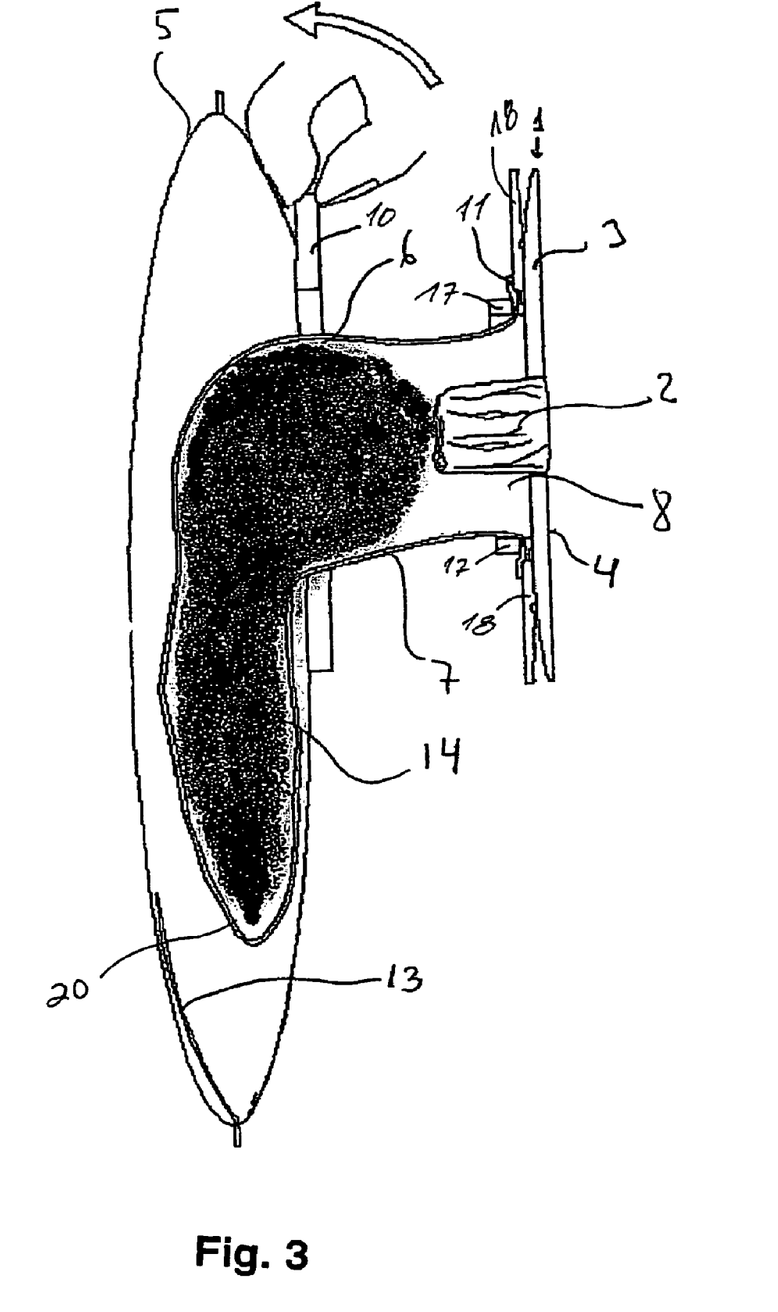
FIG. 3 shows the embodiment of FIG. 2 during the first step of detachment.

In FIG. 3 is shown the embodiment shown in FIG. 2 at the end of the service period during detachment of the receiving member and with the inner bag liner in a stretched state with the its contents 14 received from the stoma. The cover 13 is detached and situated in the receiving bag bottom portion 22 of the receiving member or bag 5, which is detached from the base plate. The inner bag liner is still attached to the base plate and is in the course of being pulled out from the receiving member with the inner bag liner bottom portion 20 moving toward a distal-most position relative to said third hole 8, i.e., moving toward the receiving bag bottom portion 22.

Figure 4:
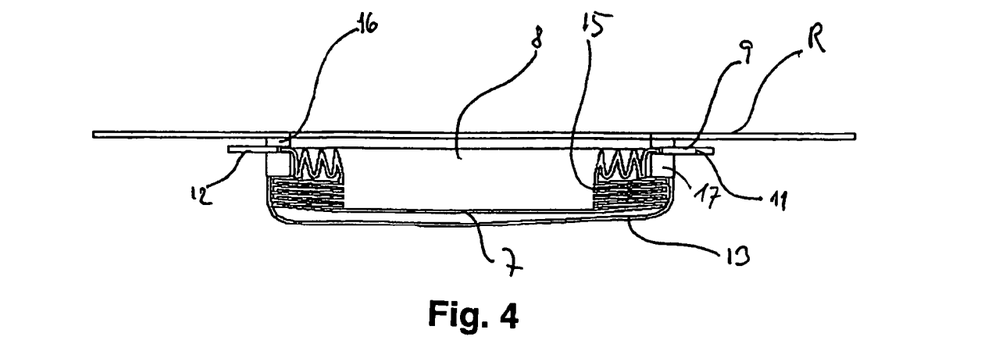
FIG. 4 shows an embodiment of a disposable inner bag liner of the invention.
Figure 5:
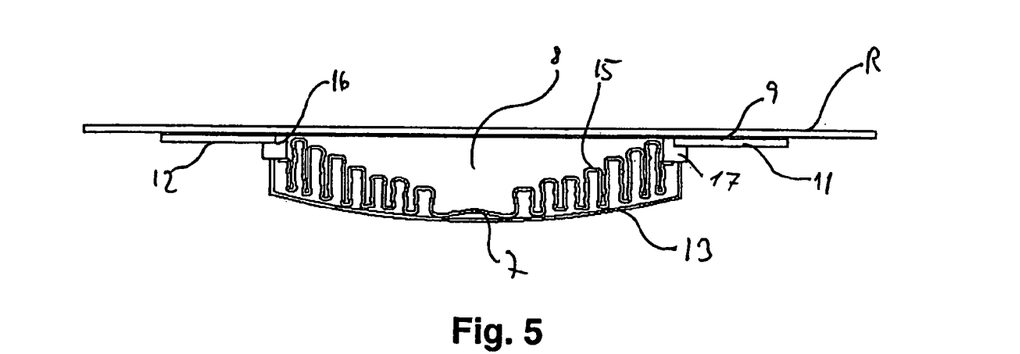
FIG. 5 shows another embodiment of a disposable inner bag liner of the invention.
Figure 6:
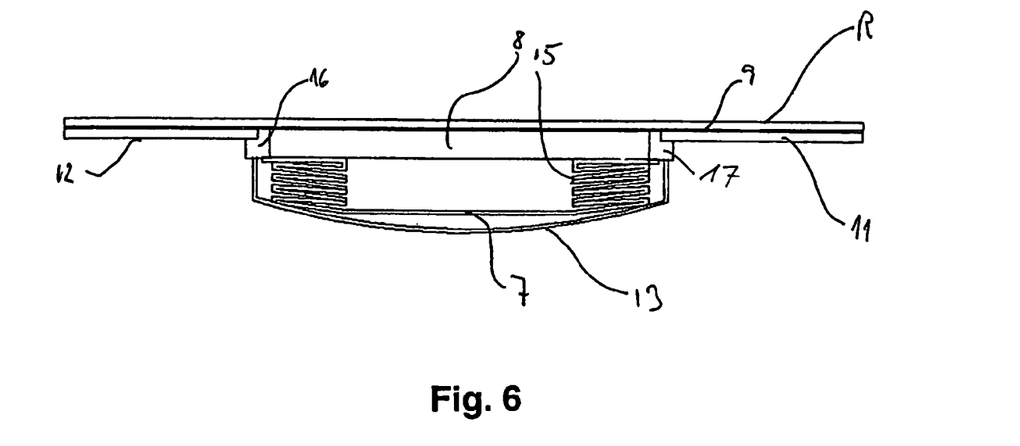
FIG. 6 shows a third embodiment of a disposable inner bag liner of the invention.

In FIGS. 4-6 are shown alternative embodiments of a disposable inner bag liner of the present invention in the form of various compacted disposable disc-shaped members for receiving effluents or waste products of the body. In FIGS. 4-6, the inner bag liners are shown in their respective compacted conditions.

The compacted disposable inner bag liner members comprise an inner bag liner 7 having a hole 8 for receiving wastes exiting the stoma, ureter or catheter and a first coupling area with a first coupling component. The first coupling component is in the form of an adhesive flange 11 projecting from the rim of the hole 8 and having a surface 9 for adhesive sealing against a surface of a base plate, the adhesive surface being covered by a release liner R. The flange 11 has an adhesive surface 12 for releasable sealing against a flange of a receiving member and is covered by a cover 13. The inner bag liner 7 and the flange 11 are secured to a ring-shaped element 16 stabilizing the rim of the hole 8. A further ring-shaped element 17 located between the cover 13 and the flange 11 is shown in FIG. 4.

The inner bag liner comprises a folded part 15 folded in different manners. In FIGS. 4 and 6 is shown an inner bag liner folded forming a combination of bellows folded radially and longitudinally and a conventional bellows for lengthwise expansion, respectively, and in FIG. 5 is shown an inner bag liner folded forming a telescopic bellows. Furthermore, different embodiments of the ring-shaped element 16 are shown in FIGS. 4-6. The ring-shaped element may be made from a single or more materials as found suitable for the purpose, typically a foam material showing the desired flexibility and is suitably made from a biodegradable foam material.

Still further, different embodiments of the flange 11 are shown. The flange shown in FIG. 4 is relatively narrow and is suitable for use together with two-piece appliances, especially two-piece appliances comprising matching coupling rings for attachment of a receiving member to the base plate, for which purpose, it is suitable that the flange is not interfering with the coupling area of the coupling rings. The embodiments shown in FIGS. 5 and 6 have broader flanges and are suitable for use together with two-piece appliances comprising matching adhesive flanges for attachment of a receiving member to the base plate or together with one-piece appliances.

Thus, the disc-shaped member of the invention may in one embodiment comprise the elements a)-f) starting from the side of the cover:

a) A relatively large transparent release liner (R) rendering it possible to see through the release liner during assembling the disc-shaped member and a receiving member to ascertain whether the disc-shaped member is located correctly (centrally) before the disc-shaped member is brought into sealing contact with flange of the receiving member.

The release liner may advantageously have an external diameter corresponding to the external diameter of the flange of the receiving member.

b) A flexible and biodegradable or water-soluble adhesive located on the surface of the ring-shaped member (16) and or the flange (11) facing a base plate for securing the inner bag liner to the base plate during removal of the receiving member, c) A flange (11) made from a biodegradable or water-soluble material such as a foam material. This flange suitably shows releasing properties at the surface (12) enabling a releasable sealing against the adhesive of the flange (10) of the receiving member. Thus, the disc-shaped member may be repositioned on the flange (10) if necessary, and is secured to the flange of the receiving member so that the user does not risk losing the disc-shaped member during application of the receiving member to the base plate, d) A folded, biodegradable or water-soluble inner bag liner (7), e) A further ring-shaped element (17) which together with the hole (6) of the receiving member ensures a centering of the disc-shaped member, and f) A biodegradable or water-soluble protecting cover (13).

In this embodiment, the risk of damaging the adhesive at the flange of the receiving member is reduced to a very high degree as the surface (12) of the flange (11) shows release-properties rather than adhesive properties.

In an alternative embodiment the disc-shaped member of the invention may comprise the following elements starting from the side of the release liner:

1) A relatively large transparent release liner (R) as stated above,

2) A biodegradable or water-soluble flange (11), e.g. a flange of foam, having a larger diameter and so as to allow adhesive engagement in the first coupling area (9) of the surface with at least a part the adhesive flange (18). This flange suitably shows releasing properties at the surface (12) as stated above, 3) A folded, biodegradable or water-soluble inner bag liner (7), and 4) A biodegradable or water-soluble protecting cover (13).

When using an appliance according to the invention, typically the following steps are carried out:

Step 1: Applying and sealing the disc-shaped member to the flange of the receiving member. The diameter of the release liner suitably corresponds to the diameter of the coupling flange of the receiving member for facilitating the location using the rims of the flange and of the release liner for centering the disc-shaped member.

Alternatively, the flange of the disc-shaped member is transparent and has a diameter greater than the hole of the receiving member, and in this case the transparency of the release liner is utilised for ascertaining that the flange has sufficient contact to the coupling flange of the receiving member.

Step 2: After securing the disc-shaped member to the receiving member, the release liner is removed and the cover is suitably detached from the flange of the disc-shaped member by pressure from, e.g., a finger for unfolding the inner bag liner sufficiently to accommodate the stoma in question, and the receiving member is attached to the base plate in the conventional manner according to the type of coupling component being used.

Step 3: The inner bag liner is automatically unfolded gradually according to the output from the stoma. The first output from the stoma will contact the inner bag liner at the bottom, which again will reduce the risk of "pancaking".

The inner bag liners of the state of the art are applied in an unfolded state and this will increase the risk of "pancaking", especially when used for colostomies as the output comprises very little water and will adhere to the top of the bag and not fall into the bag.

Step 4: During substitution the receiving member is detached in the usual manner and the inner bag liner is designed so as to ensure that it is easily withdrawn from inside the receiving member through the centre hole of the coupling flange.

Step 5: The adhesive at the flange of the disc-shaped member ensures that the inner bag liner stays adhered to the base plate. The inner bag liner acts as a drip-catcher and a fresh inner bag liner may be attached to the receiving member as in step 1 at leisure without risking escaping odor or soiling of the clothing by dripping output from the stoma.

Step 6: When the fresh inner bag liner and the receiving member are assembled, the used inner bag liner is detached and may be flushed in the WC using a single flush.

The base plate and the stoma may be cleaned in the usual manner and the receiving member provided with a fresh inner bag liner is applied.

The invention claimed is:

1. An ostomy appliance comprising:
 a base plate, said base plate having a first hole for receiving a stoma, ureter, or catheter and an adhesive wafer having a first surface to be attached to the wearer's abdomen, back, or chest;
 a receiving bag releasably and reattachably attached to the base plate, said receiving bag having a second hole for receiving wastes exiting the stoma, ureter or catheter and a receiving bag bottom portion which defines a distal-most part of said receiving bag relative to said second hole; and
 a disposable inner bag liner forming a second bag inside the receiving bag and being releasably attachable and reattachable to the base plate in a first coupling area by a first coupling component, said disposable inner bag liner having a third hole for receiving wastes exiting the stoma, ureter or catheter and the receiving bag being releasably and reattachably attachable to the base plate by a second coupling component, the first coupling component being in the form of an adhesive flange projecting from the rim of the third hole and having a surface for releasable sealing against a second surface of the base plate facing away from the user, said inner bag liner having folds along a plurality of folding lines such that said inner bag liner is compacted lengthwise prior to use, said folds being provided between the third hole and an inner bag liner bottom portion which defines a distal-most part of the inner bag liner relative to the third hole both when the inner bag liner is folded and when the inner bag liner is fully unfolded inside the receiving bag to reach a distal-most position relative to said third hole so that, when the bag is empty and in said compacted condition, said inner bag liner bottom portion is in a folded position adjacent said third hole such that initial wastes exiting the stoma, ureter or catheter will push against said inner bag liner bottom portion thus causing said folds to unfold so that said inner bag liner bottom portion moves away from said folded position adjacent the third hole to said distal-most position relative to said third hole as the inner bag liner is filled, a closed end of the compacted inner bag liner being provided with a cover to retain said inner bag liner in said compacted condition prior to use.

2. The ostomy appliance as claimed in claim 1 wherein the second coupling component is in the form of an adhesive flange projecting from the rim of the second hole and having a surface for adhesive sealing against the second surface of the base plate, said first and second coupling components being configured to allow the inner bag liner to be removed and replaced with a new inner bag liner while reusing the receiving bag.

3. The ostomy appliance as claimed in claim 2 wherein an outer diameter of the first coupling component is greater than an inner diameter of the second coupling component.

4. The ostomy appliance as claimed in claim 2 wherein a peel strength of the adhesive sealing of the first coupling component is greater than a peel strength of the second coupling component.

5. The ostomy appliance as claimed in claim 1 wherein the second coupling component is in the form of one or more coupling rings and wherein an outer diameter of the first coupling component is smaller than an inner diameter of the second coupling component.

6. The ostomy appliance as claimed in claim 1 wherein the inner bag liner is provided with a membrane allowing intestinal gas to escape but is impermeable to liquids.

7. An ostomy appliance comprising:
an adhesive wafer, said adhesive wafer having a first hole for receiving a stoma, ureter, or catheter, said adhesive wafer having a first surface to be attached to the wearer's abdomen, back, or chest;
a receiving bag attached to the adhesive wafer, said receiving bag having a second hole for receiving wastes exiting the stoma, ureter or catheter and a receiving bag bottom portion which defines a distal-most part of the receiving bag relative to said second hole; and
a disposable inner bag liner forming a second bag inside the receiving bag and being releasably and reattachably attachable to the adhesive wafer by a coupling component, said disposable inner bag liner having a third hole for receiving wastes exiting the stoma, ureter or catheter, said coupling component being in the form of an adhesive flange projecting from the rim of the third hole and having a surface for releasable and reattachable sealing against a first surface of the adhesive wafer, and said inner bag liner having folds along folding lines such that said inner bag liner is compacted lengthwise prior to use, said folds being provided between the third hole and an inner bag liner bottom portion which defines a distal-most part of the inner bag liner relative to the third hole both when the inner bag liner is folded and when said inner bag liner is fully unfolded inside the receiving bag to reach a distal-most position relative to said third hole so that, when the inner bag liner is empty and in said compacted condition, said inner bag liner bottom portion is in a folded position adjacent said third hole such that initial wastes exiting the stoma, ureter or catheter will push against said inner bag liner bottom portion thus causing the folds to unfold so that said inner bag liner bottom portion moves away from said folded position adjacent the third hole to said distal-most position relative to said third hole as the liner is filled, a closed end of the compacted inner bag liner being provided with a cover to retain said inner bag liner in said compacted condition prior to use.

8. The ostomy appliance as claimed in claim 1 wherein the inner bag liner when compacted lengthwise forms a disc-like structure having an outer diameter less than the inner diameter of the first coupling component.

9. The ostomy appliance as claimed in claim 1 wherein the folding of said liner along said folding lines forms a bellows.

10. The ostomy appliance as claimed in claim 1 wherein the folding of said liner along said folding lines forms a telescopic bellows.

11. A disposable inner bag liner having an open end for receiving effluents or waste products of the body and for use together with an ostomy appliance having an adhesive wafer to be attached to the wearer's abdomen, back, or chest and a receiving bag having a receiving bag hole for receiving wastes exiting the stoma, ureter or catheter, said disposable inner bag liner comprising a liner hole in said open end for receiving wastes exiting the stoma, ureter or catheter and having a closed end being capable of forming a bag inside the receiving bag, an adhesive flange projecting from the rim of the liner hole and having a surface for releasable sealing against a surface of the adhesive wafer, said inner bag liner having folds along folding lines such that said inner bag liner is compacted lengthwise prior to use, said folds being provided between the liner hole and an inner bag liner bottom portion which defines a distal-most part of the inner bag liner relative to said liner hole both when the inner bag liner is folded and when said inner bag liner is fully unfolded inside the receiving bag to reach a distal-most position relative to said liner hole so that, when the inner bag liner is empty and in said compacted condition, said inner bag liner bottom portion is in a folded position adjacent said liner hole such that initial wastes exiting the stoma, ureter or catheter will push against said inner bag liner bottom portion thus causing said folds to unfold so that said inner bag liner bottom portion moves away from said folded position adjacent the liner hole to said distal-most position relative to said liner hole as the liner is filled, said closed end of the compacted inner bag liner being provided with a cover that retains said inner bag liner in said compacted condition prior to use.

12. The disposable inner bag liner as claimed in claim 11 wherein the inner bag liner is provided with a membrane allowing intestinal gas to escape from the inner bag liner but is impermeable to liquids.

13. A method of applying to an ostomate an ostomy appliance comprising a base plate, said base plate having a first hole for receiving a stoma, ureter, or catheter and an adhesive wafer having a first surface to be attached to the wearer's abdomen, back, or chest; a receiving bag releasably and reattachably attachable to the base plate, said receiving bag having a second hole for receiving wastes exiting the stoma, ureter or catheter and a receiving bag bottom portion which defines a distal-most part of the receiving bag relative to said second hole; and a disposable inner bag liner forming a second bag inside the receiving bag and being releasably and reattachably attachable to the base plate, said disposable inner bag liner having a third hole for receiving wastes exiting the stoma, ureter or catheter, said inner bag liner being compacted lengthwise by folds along folding lines to form a disc-like structure, said folds being provided between said third hole and an inner bag liner bottom portion which defines a distal-most part of the inner bag liner relative to the third hole both when the inner bag liner is folded and when said inner bag liner is fully unfolded inside the receiving bag to reach a distal-most position relative to said third hole so that, when the inner bag liner is empty and in said compacted condition, said inner bag liner bottom portion is in a folded position adjacent said third hole such that initial wastes exiting the stoma, ureter or catheter will push against said inner bag liner bottom portion causing said folds to unfold so that said inner bag liner bottom portion moves away from said folded position adjacent the third hole to said distal-most position as the liner is filled, said inner bag liner being releasably and reattachably attachable to the base plate in a first coupling area by a first coupling component and the receiving bag being releasably and reattachably attachable to the base plate by a second coupling component, said first coupling component being in the form of an adhesive flange projecting from the rim of the third hole and having a surface for adhesive sealing against a second surface of the base plate facing away from the user, said method comprising:

locating the stoma and applying the base plate;

locating the inner bag liner and securing said inner bag liner in said compacted condition by placing a cover on a closed end of said inner bag liner, said cover being removed in use of said inner bag liner by automatic unfolding of said bag liner in response to receipt of waste exiting said stoma, ureter or catheter entering said third hole of said inner bag liner;

applying and sealing the inner bag liner to the first coupling area;

removing a release liner covering said first coupling component; and     attaching the receiving member to the base plate.

\* \* \* \* \*